(12) United States Patent
Amitai et al.

(10) Patent No.: US 10,433,745 B1
(45) Date of Patent: Oct. 8, 2019

(54) HANDHELD ECG MONITORING SYSTEM WITH FAULT DETECTION

(71) Applicant: Ticker Medical Ltd, Ramat Gan (IL)

(72) Inventors: David Amitai, Ramat Gan (IL); Assaf Amitai, Cambridge, MA (US)

(73) Assignee: Ticker Medical Ltd, San Ramon, CA (US)

( * ) Notice: Subject to any disclaimer, the term of this patent is extended or adjusted under 35 U.S.C. 154(b) by 0 days.

(21) Appl. No.: 16/191,320

(22) Filed: Nov. 14, 2018

(51) Int. Cl.
*A61B 5/0404* (2006.01)
*A61B 5/0408* (2006.01)
*A61B 5/00* (2006.01)
*A61B 5/0432* (2006.01)
*A61B 5/04* (2006.01)

(52) U.S. Cl.
CPC ........ *A61B 5/0404* (2013.01); *A61B 5/04085* (2013.01); *A61B 5/6823* (2013.01); *A61B 5/0006* (2013.01); *A61B 5/04017* (2013.01); *A61B 5/0432* (2013.01); *A61B 5/6843* (2013.01)

(58) Field of Classification Search
CPC .......................... A61B 5/0404; A61B 5/04085
USPC ......................................................... 600/509
See application file for complete search history.

*Primary Examiner* — Nadia A Mahmood
(74) *Attorney, Agent, or Firm* — Calvin B. Ward (57) ABSTRACT

An ECG system and a method for operating a handheld device that provides input to an ECG system are disclosed. The handheld device has a plurality of receiving channels. Each receiving channel includes an electrode that is adapted for receiving electrical signals from a patient's body when the electrode is pressed against the patient's body at a predetermined location on the patient's body. The method includes monitoring an output signal from each of the channels for any of a plurality of invalid signal conditions during a period of time in which the output signal is used to generate a standard lead or precordial lead trace, signaling a user that the handheld device is improperly positioned on the patient's body, and instructing the user on how to correct a placement of the handheld device based on the detected invalid signal condition.

14 Claims, 11 Drawing Sheets

HANDHELD ECG MONITORING SYSTEM WITH FAULT DETECTION

BACKGROUND

Electrocardiography provides a set of standardized tests that are used for diagnosing abnormalities in the heart function of a patient. The standardized measurements record the potentials between various standard locations on the patient's body by placing electrodes in contact with the standard locations on the patient's body and recording potentials at the standard locations as a function of time. Most physicians are trained to read these graphs, which are often referred to as traces, as part of regular checkups or when a patient is exhibiting symptoms that may be caused by an underlying heart problem.

The standard twelve leads in an ECG test are divided into two groups, referred to as the standard leads and the precordial leads. The leads are generated by connecting ten electrodes to the patient's body and measuring the potentials between various ones of the leads or combinations of the leads as a function of time. In a clinical setting, the electrodes have adhesive pads for attaching the electrodes to the patient's body on the hands, feet, and six locations on the patient's chest, and the test is administered by a trained professional.

Unfortunately, the patient is often away from the clinical setting when a cardiovascular event is suspected. There are basically two solutions to this problem. The first involves connecting the electrodes to the appropriate locations on the patient's body adhesively and providing the patient with a portable unit that records the ECG traces. This type of solution generates traces that are essentially the same as those generated in the clinical setting; however, wearing the electrodes over a significant period of time presents numerous challenges if the patient also wishes to pursue a normal life.

The second solution involves providing the patient with a handheld unit that the patient uses to record various traces by holding the unit in the patient's hands and touching electrodes on the outside of the unit to various locations on the patient's body during the recording of the signals. Numerous devices have been proposed in which the handheld unit includes either three or four electrodes on the outer surface of the unit which the patient holds such that either one or both hands touch the electrodes while the patient places the remaining electrode at various points on the patient's body that are determined by the specific test or group of tests that are to recorded.

While these handheld devices allow the patient to perform one or more tests without having to affix electrodes adhesively to the patient's body, the resulting tests are not always a good approximation to the standard tests and present challenges when attempting to diagnose the patient based on these tests; however, even in the case of non-standard tests, these devices can be used to provide data on whether or not the patient's heart function has changed from the last tests performed with the handheld device.

All of these devices require the patient to maintain the electrical connection between the patient's skin and the electrodes on the handheld device for a period of seconds while the potentials on the electrodes are recorded. If the device loses contact between an electrode and the patient's skin, an abnormal recording will result. Since the patient is typically not a trained medical technician operating in a clinical setting, guaranteeing that the required pressure is applied between the patient's body and the electrodes in question presents significant challenges.

SUMMARY

The present invention broadly includes a ECG system and a method for operating a handheld device that provides input to an ECG system. The handheld ECG acquisition device has a plurality of receiving channels. Each receiving channel includes an electrode that is adapted for receiving electrical signals from a patient's body when the electrode is pressed against the patient's body at a predetermined location on the patient's body. The method includes monitoring an output signal from each of the channels for any of a plurality of invalid signal conditions during a period of time in which the output signal is used to generate a standard lead or precordial lead trace, signaling a user of the handheld ECG acquisition device that the handheld ECG acquisition device is improperly positioned on the patient's body, and instructing the user on how to correct a placement of the handheld ECG acquisition device based on the detected invalid signal condition and the channel in which the invalid signal condition was detected.

In one aspect of the invention, the plurality of invalid signal conditions includes a harmonic of AC line frequency, a constant voltage having an amplitude greater than a first threshold, or a signal strength that increases faster than a second threshold.

In another aspect of the invention, instructing the user on how to correct the placement of the handheld ECG acquisition device includes displaying a graphic of the correct placement on a display screen that is coupled to the handheld ECG acquisition device.

In another aspect of the invention, instructing the user on how to correct the placement of the handheld ECG acquisition device includes aural instructions generated by a speaker that is coupled to the handheld ECG acquisition device.

In another aspect of the invention, instructing the user on how to correct the placement of the handheld ECG acquisition device includes generating an audible tone indicating an invalid signal is detected.

In another aspect of the invention, the handheld ECG acquisition device is adapted to record a plurality of tests in a predetermined sequence, each test includes recording signals from the electrodes with one of the electrodes located at a different point on the patient corresponding to that test for a predetermined recording time, and the handheld ECG acquisition device detects a transition from an invalid signal to a valid signal after a previous test has been completed to signal a start of a new test in the predetermined sequence if all of the tests have not been completed.

An ECG recording system according to the present invention broadly includes a handheld ECG acquisition device characterized by a plurality of electrodes on an outer surface of the handheld ECG acquisition device. Each electrode is adapted to provide an electrical connection to a corresponding location on a patient's skin when the electrode is pressed against the corresponding location, each electrode being connected to a corresponding interface circuit for amplifying an electrical signal received by the electrode to generate an output signal. A receiving processor is adapted to receive the output signal from each of the plurality of electrodes, the receiving processor monitoring each output signal for one of a plurality of invalid signal conditions and interrupting a recording of the output signals if an invalid signal is detected.

In another aspect of the invention, the receiving processor is physically connected to the handheld ECG acquisition device.

In another aspect of the invention, the receiving processor is separate from the handheld ECG acquisition device and receives the output signals by a wireless link.

In another aspect of the invention, the receiving processor generates an ECG recording selected from the group consisting of standard lead traces and precordial traces.

In another aspect of the invention, the receiving processor notifies a user if an invalid signal is detected.

In another aspect of the invention, the receiving processor provides instructions on how to correct a position of the handheld ECG acquisition device when an invalid signal is detected.

In another aspect of the invention, one of the electrodes includes a metal layer on one surface of a printed circuit board and the interface circuit corresponding to that electrode includes an integrated circuit mounted on another surface of the printed circuit board connected to the metal layer by a conducting via through the printed circuit board.

In another aspect of the invention, the handheld ECG acquisition device is adapted to record a plurality of tests in a predetermined sequence, each test includes recording signals from the electrodes with one of the electrodes located at a different point on the patient corresponding to that test for a predetermined recording time, and wherein the handheld ECG acquisition device detects a transition from an invalid signal to a valid signal after a previous test has been completed to signal a start of a new test in the predetermined sequence if all of the tests have not been completed.

DETAILED DESCRIPTION

Handheld ECG measurement systems can be viewed as having two basic components. The first provides the electrodes for measuring the voltages on the skin of the patient and the interface circuitry to amplify the voltages to levels that allow the signals to be processed by the second component. The second component processes the amplified signals to form the recordings of the heart's electric activity. In the case of the standard lead measurements, each of the six standard lead traces is generated by forming sums and differences of the signals on particular electrodes. In the case of the precordial measurements, the difference in potential between the sum of the signals from each hand, the left leg and the signal from a particular point on the chest is generated for each of the six points on the chest.

To simplify the following discussion, the first component will be referred to as the handheld ECG acquisition device. The handheld ECG acquisition device has two or more electrodes on the outer surface of the device for detecting voltages on the patient's skin. The voltages, in general, are very low. Hence, the handheld ECG acquisition device will typically include some form of amplifier to condition the signal so that the signal can be processed by more conventional circuitry such as analog-to-digital converters (ADCs) or communicated to the second component. Each electrode that measures a signal on the skin and the conditioning circuitry will be referred to as a channel. The handheld ECG acquisition device may also include one or more additional electrodes or other components.

The second component will be referred to as the receiving processor in the following discussion. The receiving processor receives the conditioned signals from the handheld ECG acquisition device and generates the standard ECG traces from those conditioned signals. The receiving processor can be separate from the handheld ECG acquisition device or the two components can be integrated in the same physical device. U.S. Pat. No. 8,082,025, issued on Dec. 20, 2011 describes a system in which the two components are combined in a smart phone with the electrodes on the outer surface of the smart phone. U.S. Pat. No. 10,092,202, issued on Oct. 9, 2018 describes a system in which the handheld ECG device is separate from the receiving processor and communicates with the receiving processor via a wireless link. Separated systems have the advantages of combining the computing power of the smart phone or local computer with a handheld ECG device of a size that can be easily carried on a key ring or the like.

The manner in which the present invention provides its advantages can be more easily understood with reference to a specific handheld device which is described in U.S. Pat. No. 10,092,202, issued on Oct. 9, 2018, which is hereby incorporated by reference. Both types of devices require the user to contact the patient's hands and body at specific locations with sufficient force to receive valid signals during the period of time the signals are being recorded.

Figure 1:
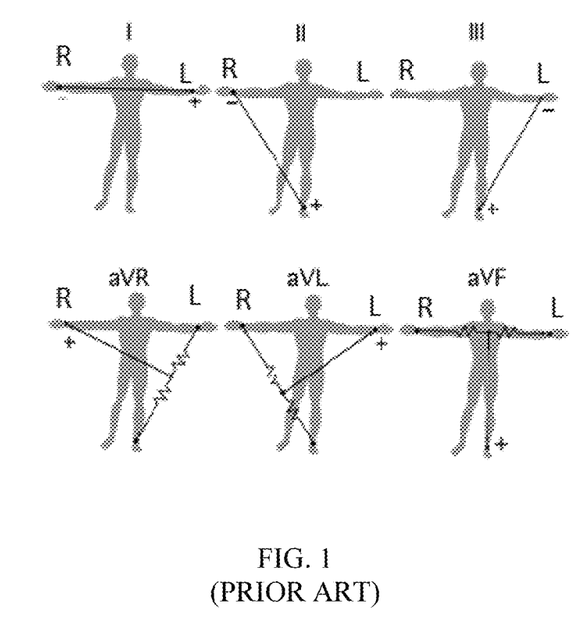
FIG. 1 illustrates the placement of electrodes and the signals that are measured in the "standard lead measurements" that are six of the twelve recordings provided in a conventional twelve-lead ECG.

Refer to FIG. 1, which illustrates the placement of electrodes and the signals that are measured in the "standard lead measurements" that are six of the twelve recordings provided in a conventional twelve-lead ECG. The standard lead measurements provide recordings as a function of time of the potentials between pairs of electrodes that are connected to the patient's body. For example, the first standard lead measurement, which is often referred to as the lead I measurement, or just Lead I, consists of the difference in potential measured between the left and right wrists of the patient, as a function of time. Similarly, the lead II measurement, or Lead II, consists of the difference in potential, as a function of time, measured between the left leg and the right wrist of the patient. Lead I consists of the difference in potential, as a function of time between the left leg and the left wrist of the patient. The remaining three leads, aVR, aVL, and aVF are differences between the potential of one limb and the average potential of another two limbs Denote the potential at the right wrist or hand by $\Phi_r$, the potential at the left wrist or hand by $\Phi_l$, and the potential at the left leg by $\Phi_f$. The first three standard leads or traces are given by $$I = \Phi_l - \Phi_r,$$

$$II = \Phi_f - \Phi_r, \text{ and}$$

$$III = \Phi_f - \Phi_l = II - I \quad (1)$$

As noted above, these signals are each functions of time. In the following discussion, the Lead I signal as a function of time will be referred to as the hand signal. The Lead II signal as a function of time will be referred to as the leg signal.

Three additional traces are generated by utilizing weighted sums and differences of the Lead I and II signals, namely $$aVR = \Phi_r - (\Phi_l + \Phi_f)/2 = -(I + II)/2,$$

$$aVL = \Phi_l - (\Phi_r + \Phi_f)/2 = I - II/2, \text{ and}$$

$$aVF = \Phi_f - (\Phi_r + \Phi_l)/2 = II - I/2. \quad (2)$$

Figure 2:
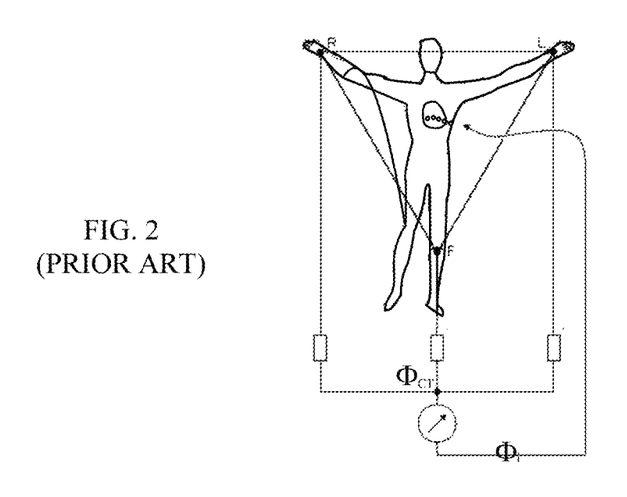
FIG. 2 illustrates the measurement of the precordial traces.

The remaining six traces of the conventional twelve-lead ECG are the precordial traces ($V_1$-$V_6$). Refer now to FIG. 2, which illustrates the measurement of the precordial traces. In the conventional precordial measurements, each trace is generated by forming the average of the potentials at the right and left wrists and the left leg (this averaged potential is known as Wilson's Central-Terminal $\Phi_{CT}$) and then measuring the difference between a potential, $\Phi_i$, detected by an electrode at a corresponding point on the patient's chest and $\Phi_{CT}$. A different predetermined point on the chest is used for each of the six traces:

$$V_i = \Phi_i - (\Phi_l + \Phi_f + \Phi_r)/3 = \Phi_i - \Phi_{CT}, \quad (3)$$

where $V_i$ (i=1 . . . 6) are the precordial leads. The average signal from the hands and leg is often referred to as the "C-terminal". It should be noted that a C-terminal signal can be generated from other locations on the three extremities in question. For example, the potentials corresponding to the leg can be measured at the foot, ankle, or upper thigh or lower abdomen. Similarly, the potentials corresponding to the "hands" can be measured any place between one of the fingers and the shoulder.

It should be noted that the traces are always measured as a difference in potential between two electrodes placed on the corresponding locations on the patient's body by utilizing differential amplifiers to form the differences of the signals in question. Ideally, this procedure eliminates the effects of common mode signals that are picked up by the patient's body such as the 50 or 60 cycle AC signals that are present in most indoor environments. Unfortunately, the magnitudes of the common mode signals are much greater than that of the heart signals that are the subject of the measurements in question, and the available differential amplifiers have a common mode rejection figure that is insufficient to eliminate all of the common mode noise in question.

To reduce the common noise, a signal that is a good approximation to a signal that would cancel the common mode signal in the patient's body is generated and then injected into the right ankle in conventional ECG measurement devices. This signal will be referred to as the common mode cancellation signal in the following discussion. The common mode cancellation signal must be injected at a location that will not interfere with the measurement of the signals from the ECG electrodes. The common mode cancellation signal reduces the common mode signal in the patient's body by canceling the common mode signal that is picked up from the patient's body, and hence, reduces the problems associated with the large difference between the common mode noise and the signals of interest, since the signals of interest no longer have a large common mode signal as part of each signal.

In the prior art, an electrode attached to the right leg is used as the injection point for the common mode cancellation signal. This does not present a significant problem with respect to the signals detected by the other electrodes, since the right ankle is far from the location of the other electrodes, and hence, any localized signal variations are dissipated by the time the cancellation signal reaches the portions of the body near the electrodes of interest. Since the C-terminal signal is an average of the potentials at widely separated points on the patient's body, the inverse of the C-terminal signal is often utilized as the common mode cancellation signal. That is, the inverse of the C-terminal signal is injected into the right ankle to reduce the common mode noise.

Figures 3A, 3B:
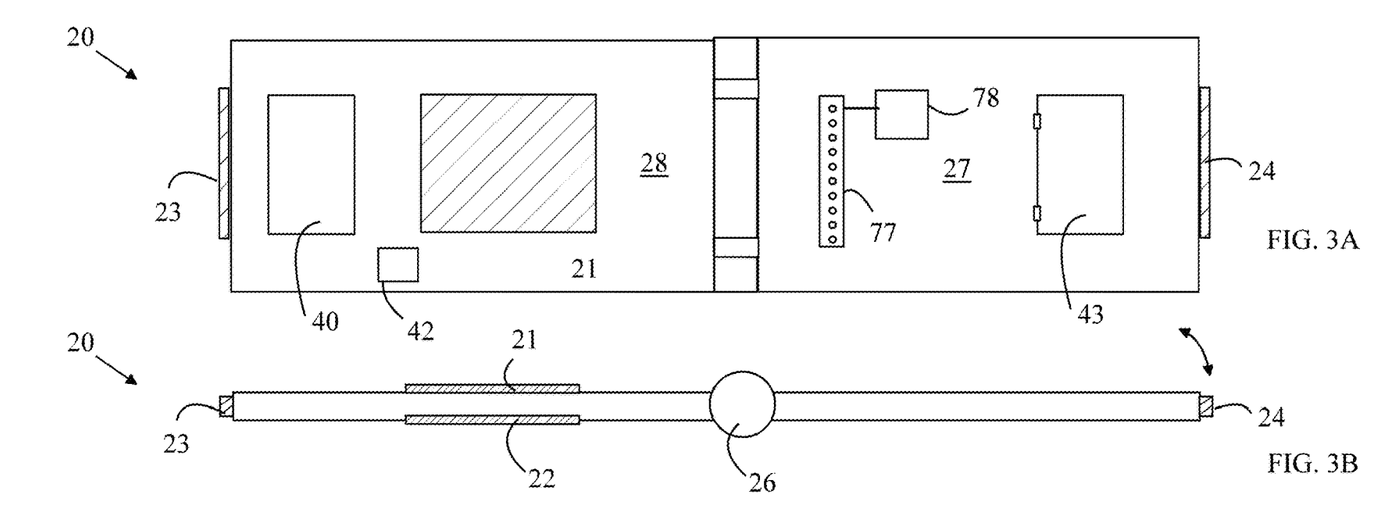
FIGS. 3A-3D illustrate one embodiment of an ECG data acquisition device.
Figure 3C:
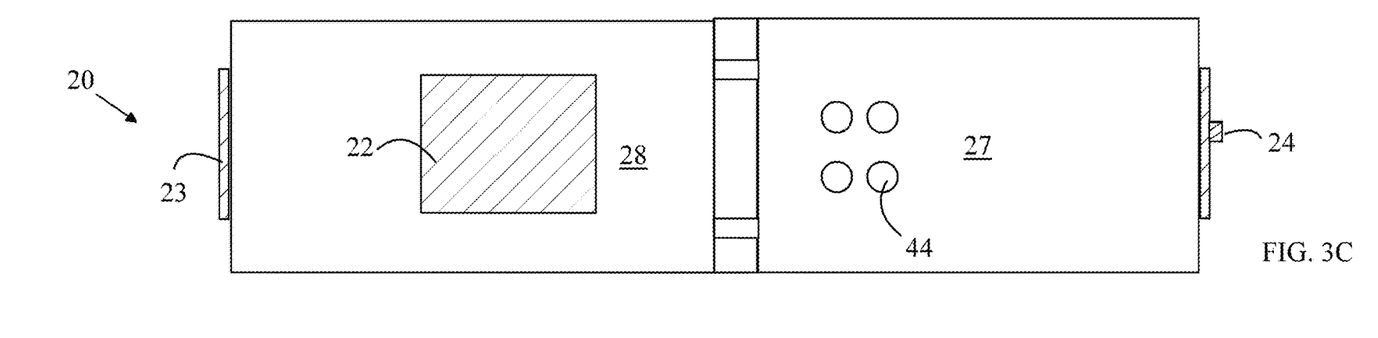
Figure 3D:
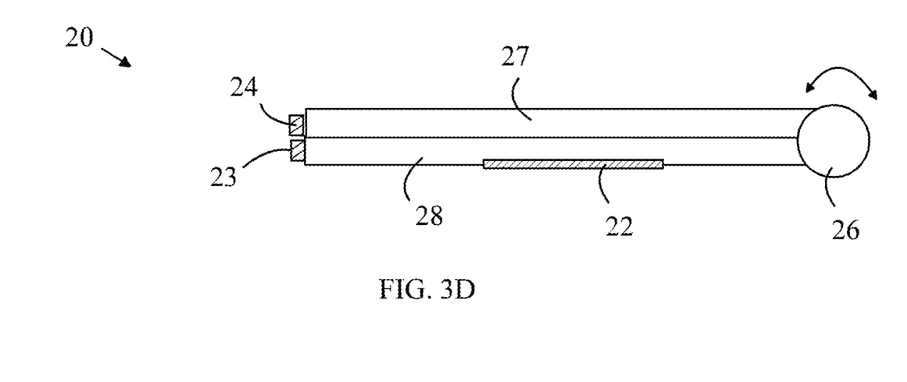

In the embodiments taught in the above-identified U.S. Pat. No. 10,092,202, the handheld device has four electrodes on the outer surface of the probe. Refer now to FIGS. 3A-3D, which illustrate one embodiment of such an ECG data acquisition device. ECG data acquisition device 20 has an extended configuration and a storage configuration. FIG. 3A is a top view of ECG data acquisition device 20 in the extended configuration; FIG. 3B is a side view of ECG data acquisition device 20 in the extended configuration, and FIG. 3C is a bottom view of ECG data acquisition device 20 in the extended configuration. FIG. 3D is a side view of ECG data acquisition device 20 in the storage configuration, which in the case of ECG data acquisition device 20 is a folded configuration. When being used to measure ECG recordings, ECG data acquisition device 20 is operated in the extended configuration. For storage, ECG data acquisition device 20 is folded.

It should be noted that providing a very small object that is carried by the user when not being used is important. If the object is large, the user will not carry it with the user. A device that is the size of a memory stick when in the storage configuration can easily be accommodated on a keychain or the like. Hence, the user is not inconvenienced by having the device with the user at all times. To facilitate communication between the ECG data acquisition device and the user, one or more buttons such as button 44 can be provided to provide user inputs into the ECG data acquisition device. These buttons can be used by the user to signal the ECG data acquisition device that the user wishes to perform a specific measurement such as one particular ECG recording.

Figure 4:
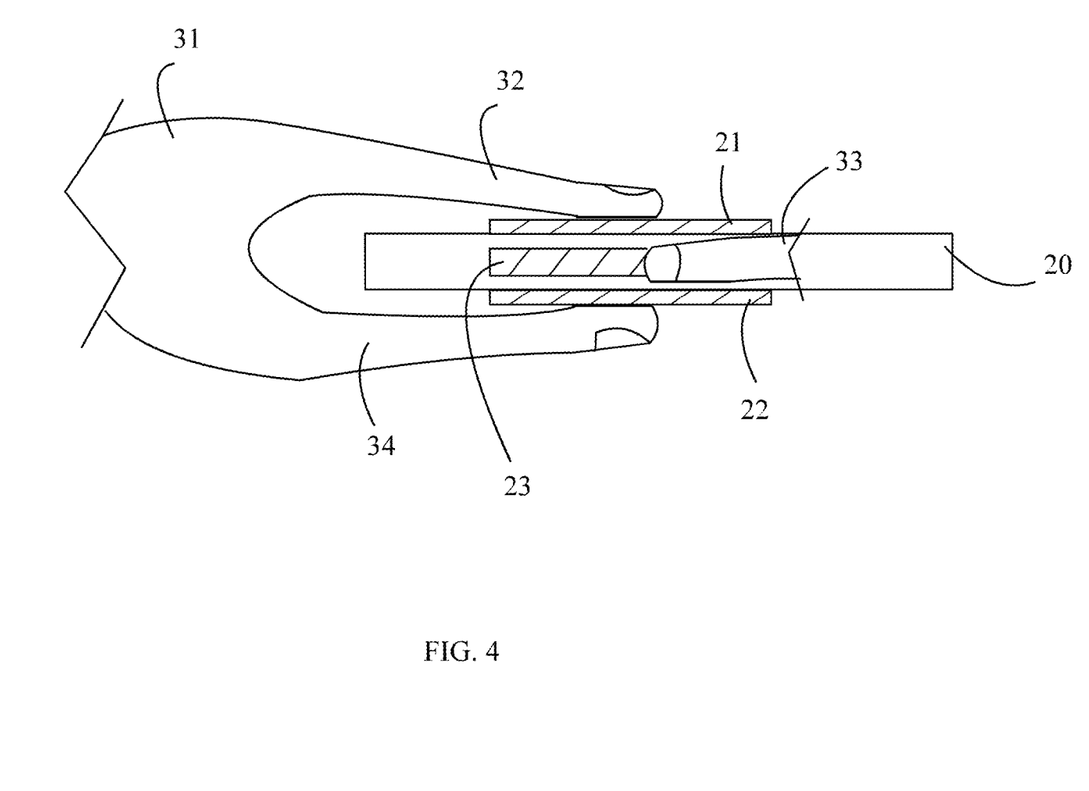
FIG. 4 is an end view of ECG data acquisition device 20.

Referring to FIGS. 3A-3D, ECG data acquisition device 20 includes four electrodes shown at 21-24, respectively. A twelve-trace ECG diagram is obtained using ECG data acquisition device 20 by holding the ECG data acquisition device with both hands and pressing electrode 24 against the appropriate place on the patient's body. Refer now to FIG. 4, which is an end view of ECG data acquisition device 20. In one embodiment, electrodes 21 and 22 are held in the right hand 31 with the thumb 32 on electrode 21 and the right index finger 34 on electrode 22. The left index finger 33 or any part of the left palm is held on electrode 23. It should be noted that electrode 22 can be touched with other fingers of the right hand besides the index finger. Electrode 21 can also be touched with other fingers or part of the right hand. Referring again to FIGS. 3A-3D, for the standard lead measurements, electrode 24 is placed against any point on the left leg or the lower abdomen. For the precordial measurements, electrode 24 is placed sequentially at each of the precordial positions on the patient's chest.

To reduce the size of the handheld device, the ECG acquisition device is constructed from two sections shown 27 and 28 that are connected by hinge 26. When not in use, the two sections are folded together.

The ECG acquisition device may optionally include other functions, such buttons 44, acoustical generator 42, and display 40 for communication between the user and the receiving processor. The ECG acquisition device can also include a connector 77 for connecting conventional ECG electrodes and/or other wired components and a compartment 43 for storing medications to be used in the event of a heart problem. Controller 78 can manage these additional functions.

As noted above, the four conventional electrodes are placed on the left and right wrists and the left and right ankles. In the system discussed above, these measurements are provided by using the potential at the right index finger, i.e., electrode 22, in place of the potential at the right wrist, the potential at the right thumb, i.e., electrode 21 in place of the potential at the right ankle, the potential at the left index finger, i.e., electrode 23, in place of the potential at the left wrist, and the potential at the left leg, i.e., electrode 24 in place of the potential at the left ankle.

The common mode cancellation signal is injected into the right thumb through electrode 21 in this embodiment of the present invention. It has been observed that using the thumb for the common mode cancellation signal injection site provides the desired cancellation of the common mode noise without significantly interfering with the measurements of the ECG recordings even though the signal from the right index finger is used to generate the ECG recordings.

To simplify the following discussion, it is useful to separate the electrodes on the surface of the handheld device into two groups. The first group consists of the electrodes that are used to read the potentials from the patient's skin at the various locations during the recordings. Depending on the particular handheld device, this group has two or three interface circuits. For example the above-described embodiments utilize three electrodes in this group. However embodiments have been suggested that have only two electrodes. While such two-electrode systems can produce ECG traces that can detect changes in an individual patient's condition from measurement to measurement, these systems typically do not reproduce standard lead measurements on which most medical diagnosis is based. However such systems can still benefit from the present invention.

The second group consists of the electrode that is used to inject the common mode cancellation signal into the patient's body.

Figure 5A:
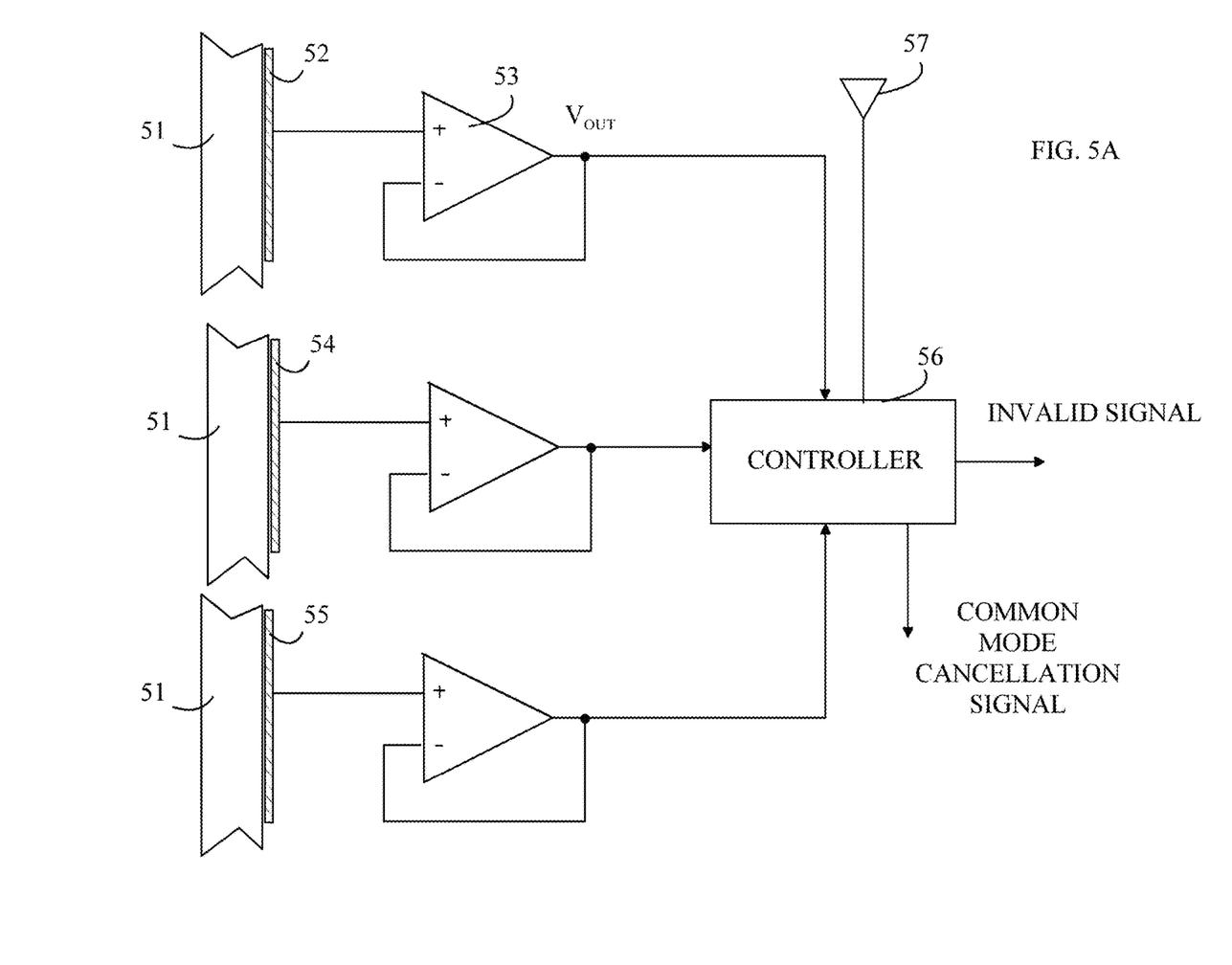
FIG. 5A illustrates the interface circuitry for a typical electrode according to one embodiment of the present invention and the first group when that electrode is in contact with the patient's skin.

Refer now to FIG. 5A, which illustrates the interface circuitry for a typical electrode according to one embodiment of the present invention and the first group when that electrode is in contact with the patient's skin. The patient's skin is shown at 51. In this example, there are three electrodes (52, 54, and 55) that receive signals from the patient's skin. One electrode connects to the index finger of one hand; one electrode connects to the index finger of the other hand, and the third electrode is placed in various locations on the patient's chest or abdomen depending on the specific ECG trace being recorded. Each electrode is connected to a corresponding amplifier such as amplifier 53.

The purpose of amplifier 53 is to lower the impedance of the circuit path from amplifier 53 to controller 56, which is typically located at some distance from the corresponding electrode without substantially amplifying any noise that is picked up by the corresponding electrode. By lowering the input impedance of electrode input to controller 56, the circuit is less sensitive to noise signals that are picked up by the signal path between controller 56 and the corresponding electrode. Accordingly, amplifier 53 preferably has a gain that is approximately one and a high input impedance.

In one aspect of the invention, amplifier 53 is located on a small circuit board that is bonded to the corresponding electrode to minimize the length of any connecting leads between the input to amplifier 53 and the corresponding electrode.

The output of amplifier 53 is communicated to a controller 56 that monitors the signals from electrodes 52, 54, and 55 for features that indicate that one or more of the electrodes is not in proper contact with the patient. In this example, controller 56 also generates the common mode cancellation signal that is connected to a fourth electrode such that the common mode cancellation signal is injected into the patient. In this embodiment, controller 56 also transmits the amplified signals to the receiving processor as discussed below over a wireless link 57.

Figure 6A:
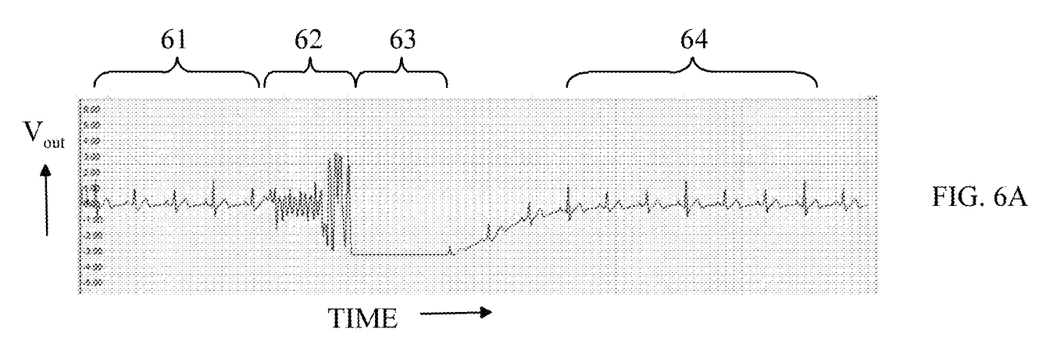
FIGS. 6A and 6B illustrate the output of amplifier 53 over time when the electrode transitions from being in contact with the patient's skin, breaks contact with the patient's skin and then is reconnected to the patient's skin.
Figure 6B:
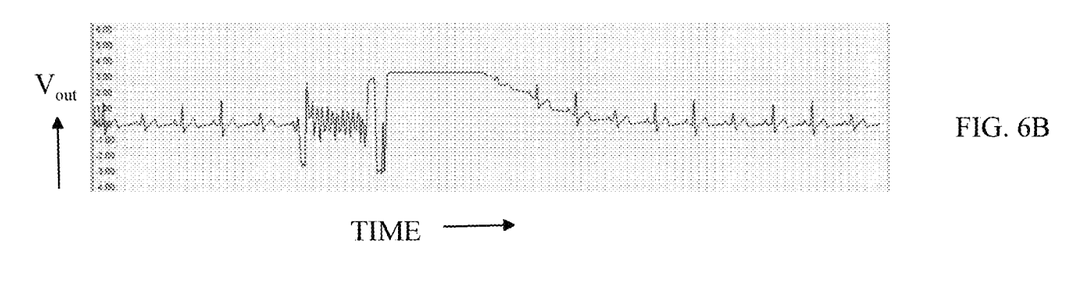

Refer now to FIGS. 6A and 6B which illustrate the output of amplifier 53 over time when the electrode transitions from being in contact with the patient's skin, breaks contact with the patient's skin and then is reconnected to the patient's skin. During the time shown at 61, the patient is maintaining sufficient pressure between the handheld device and the patient's skin to provide a good signal that can be used to make the relevant measurement in conjunction with the signals from the other electrodes. As the patient reduces the pressure on the skin, the resistance between the skin and the electrode increases, and the input to the amplifier begins to pick up power line frequencies or harmonics thereof as shown at 62. This is an invalid signal for ECG purposes. If the patient continues to relieve the pressure, the contact will be broken electrically, and the output of amplifier 53 will jump in a short period to a constant potential that is two and four times the baseline voltage as shown at 63. The jump in the base line voltage can be either in the negative direction as shown in FIG. 6A or in the positive direction as shown in FIG. 6B. If the patient now reapplies the proper amount of force between the electrode and patient's skin, the signal returns to normal as shown at 64.

The present invention monitors the output of the amplifier for invalid signal periods during the time that the patient is recording an ECG trace. For example, the present invention monitors the output of each channel for a sudden voltage change which can be either positive or negative. If the voltage jumps more than a predetermined amount in either direction within a predetermined time interval during the recording of an ECG trace, an invalid signal indication is generated. The thresholds for the positive and negative thresholds that define an invalid signal may be different. The voltage jump will last as long as the electrode is disconnected from the skin. Typically the amplitude of the voltage jump is two to four times the magnitude of the baseline voltage. As noted above, when the electrode is again pressed against the skin with sufficient force, the voltage will go back to the normal recording voltage after some recovery.

In one aspect of the invention, a large voltage swing over a short period of time also gives rise to an invalid signal detection being generated. In one exemplary embodiment, a voltage swing of greater than 3 volts over 200 milliseconds when the peak-to-peak voltages of the valid signals are less than 1 volt, after amplification, is defined to be an invalid signal.

In another aspect of the invention, the actual voltage values are compared to a range of values derived from valid signals. For example, if a valid signal has a typical voltage between −0.5V and IV, voltage values greater than +3V or less than −3V indicate invalid signals.

The present invention also monitors the output of the amplifier for the presence of harmonics of the power line frequency in the area in which it is being used that lie in the frequency range of the pulses associated with the heart activity. The presence of a harmonic of the power line frequency is detected by comparing the amplitude at the harmonic frequency with the amplitude at a frequency displaced from the harmonic frequency. For example, when the device is being used in a region in which the power line frequency is 50 Hz, the system monitors the amplitude of the output of the amplifier at multiples of 50 Hz and at frequencies that are intermediate with these frequencies. If the amplitude of the amplifier output at a harmonic frequency is greater than some predetermined value of the amplitude at the intermediate frequency, the system assumes that power line interference is present, and hence, the measurements may not be valid.

In one example, in a region in which the power line frequency is 50 Hz, the system monitors the amplitude of the amplifier output at frequencies of 75 Hz, 100 Hz, 125 Hz, and 150 Hz. If the amplitude at 100 Hz is greater than four times that at 75 Hz, it is assumed that power line interference is occurring, and an invalid signal is generated. In another example, if the amplitude at 150 Hz is greater than ten times that of the amplitude at 125 Hz, an invalid signal is generated.

In one aspect of the invention, the system also detects the local power line frequency.

The controller that monitors the recording channels and generates an invalid signal can be located at multiple locations in the system in which the handheld device having the electrodes that contact the patient's body is located. To clarify the following discussion, the handheld device having the electrodes that contact the patient's body will be referred to as the ECG acquisition device and the electrodes will be referred to as the contact electrodes. The ECG recording system typically has another component, referred to as the receiving processor that receives the signals from the interface amplifiers discussed above, communicates with the patient, and performs other functions as discussed below. The receiving processor can be a separate unit or be incorporated in the ECG acquisition device. If the two devices are separate, there is typically a link between the devices, which is preferably a wireless link; although the two devices could be tethered together by a cable such as a USB.

Figure 7:
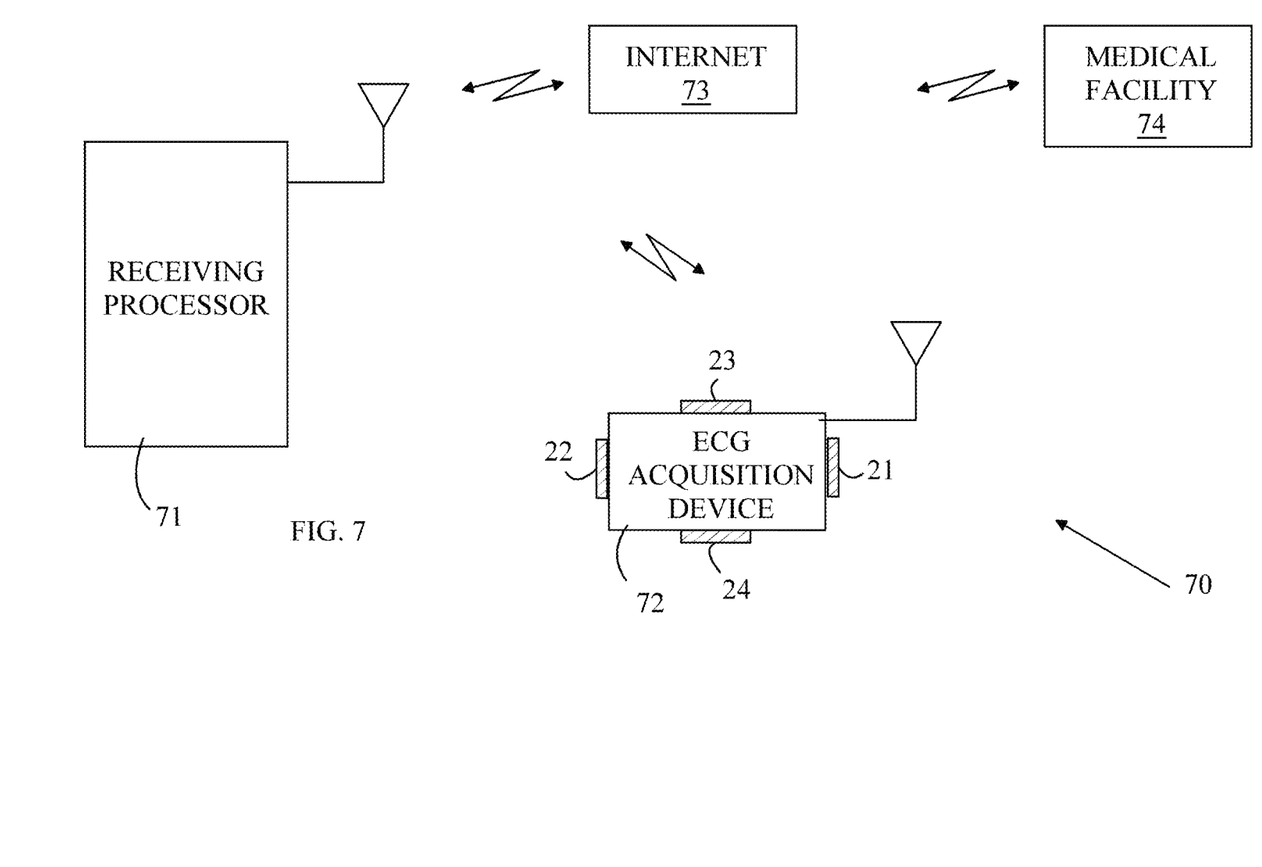
FIG. 7 illustrates a portable ECG measurement system according to one embodiment of the present invention.

To simplify the following discussion, it will be assumed that the ECG acquisition device and the receiving processor are physically separated devices that communicate via a wireless link. Refer now to FIG. 7, which illustrates a portable ECG measurement system according to one embodiment of the present invention. Measurement system 70 includes an ECG acquisition device 72 having four electrodes (21-24) that are brought into contact with the patient's body, three of the electrodes contact the patient's hands and the fourth electrode 24 contacts the patient's body at locations that depend on the specific trace being recorded. The common mode rejection signal is injected into electrode 21.

The channel amplifiers discussed above are located in ECG acquisition device 72. The controller that monitors the output of these amplifiers could be located either in ECG acquisition device 72 or in receiving processor 71. In one aspect of the invention, the controller is located in receiving processor 71 to minimize the power that must be stored in ECG acquisition device 72.

Receiving processor 71 needs to be able to perform a number of functions. In principle, many of these functions could be performed remotely via the Internet 73 at a remote medical facility 74. However, the link with the Internet may not be available when the patient needs to record the ECG signals; hence, it is advantageous to perform the processing of the signals from the electrodes to generate a conventional set of ECG traces in either the receiving processor or the ECG acquisition device. In one aspect of the invention, receiving processor 71 is a smart phone or a local computer that is connected to ECG acquisition device 72 via a Bluetooth link. This arrangement makes use of the computing capabilities already in these devices and minimizes the power that is needed for the ECG acquisition device.

When the controller detects an invalid signal during a recording, the controller warns the patient that the patient must change the manner in which the patient is contacting the electrode associated with the invalid signal determination. The warning can be signaled from the data acquisition device or from the receiving processor. The warning can be simply an error light or a tone. In more complex embodiments, the receiving processor has a display screen on which a graphic is displayed which provides more detailed information on the nature of the error. The warning error may be displayed or sounded on both the receiving processor and the ECG acquisition device simultaneously.

Figure 8A:
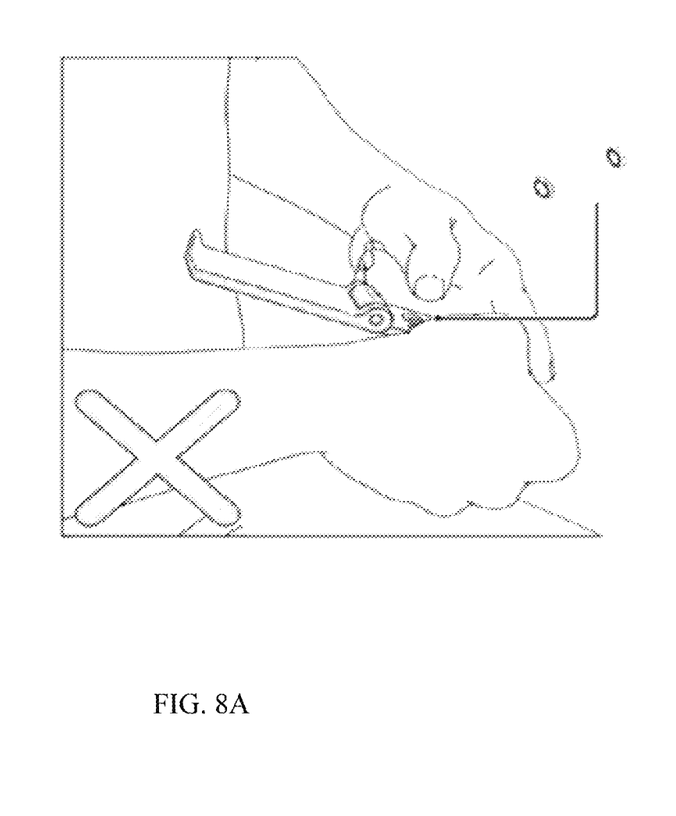
FIGS. 8A and 8B illustrate an exemplary invalid signal display in the case in which the patient is incorrectly holding and applying the ECG acquisition device during a standard lead measurement.
Figure 8B:
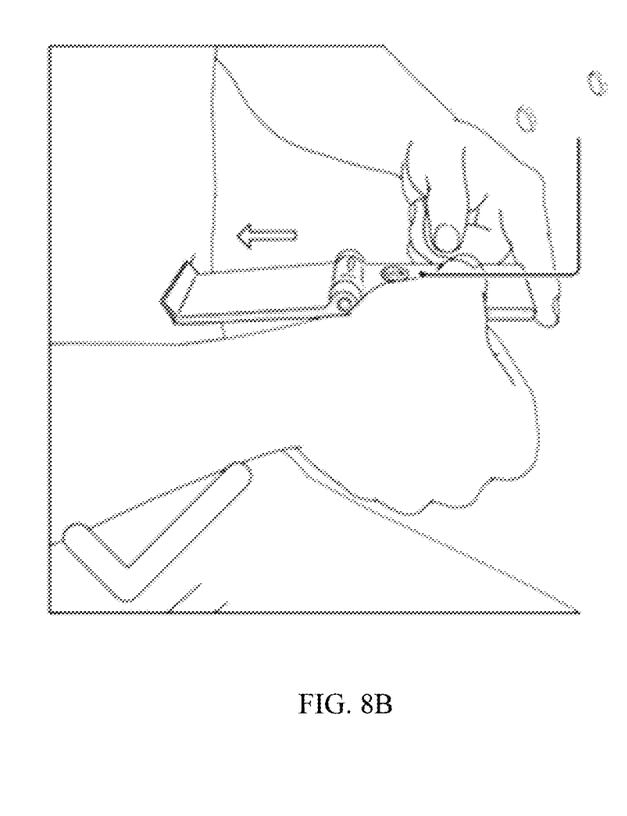

Refer now to FIGS. 8A and 8B, which illustrate an exemplary invalid signal display in the case in which the patient is incorrectly holding and applying the ECG acquisition device during a standard lead measurement. In FIG. 8A, the graphic indicates to the patient that the patient has not properly positioned that ECG acquisition device on the patient's abdomen. In addition, the ECG acquisition device includes a warning light which is also illuminated during the incorrect holding display. The correct positioning of the ECG acquisition device is provided in a second display that is shown in FIG. 8B to guide the patient in more correctly positioning the ECG acquisition device. The graphic contains a drawing indicating the correct placement of the ECG acquisition device relative to the patient's body. In addition, the invalid signal display can also provide audible instructions providing the patient with instructions as to how to improve the patient's holding of the ECG acquisition device against the patient's body. For example, the audio instructions can instruct the patient to press the device harder against the patient's abdomen if the invalid signal is associated with electrode 24. In another example, the audio instructions can instruct the patient to touch one of the other electrodes with more force and provide the identity of the electrode in question.

Figure 9:
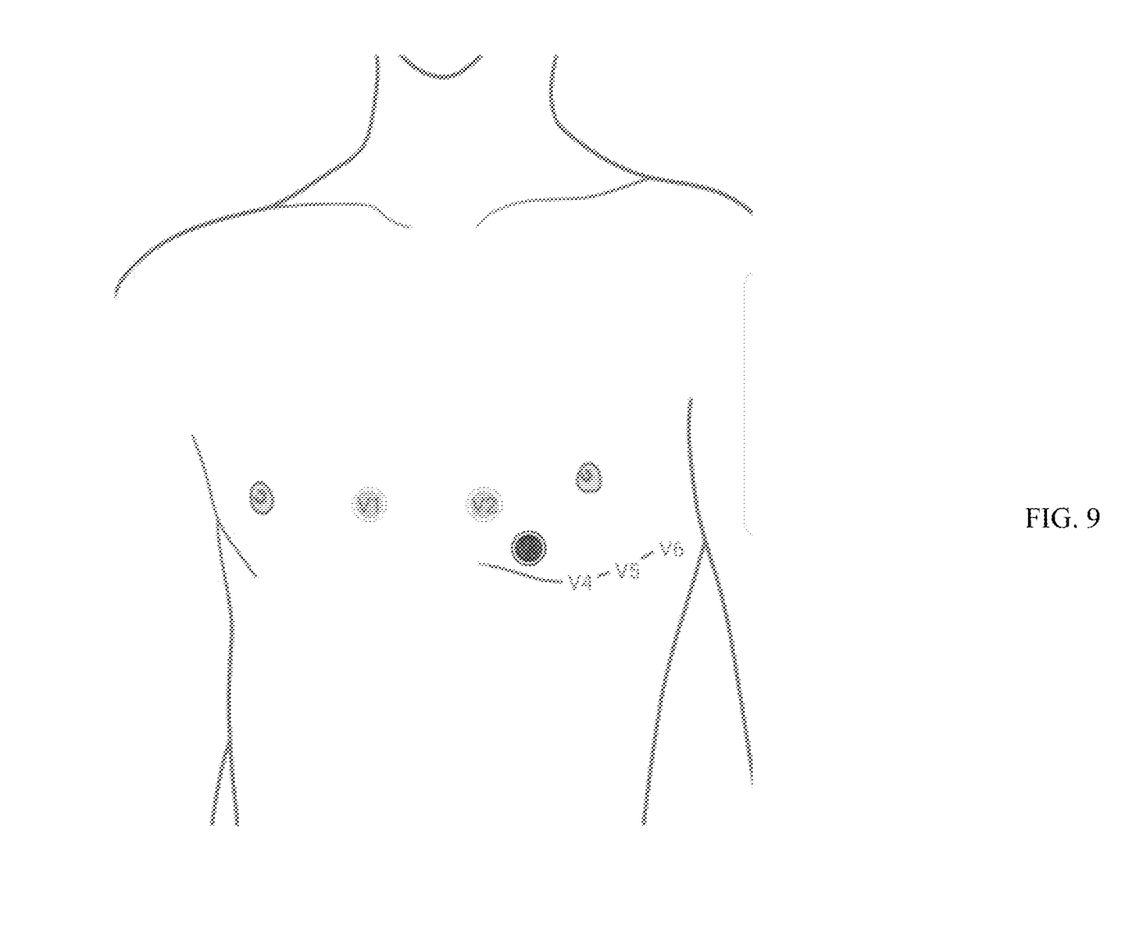
FIG. 9 illustrates an invalid signal display during a precordial trace recording.

Refer now to FIG. 9, which illustrates an invalid signal display during a precordial trace recording. In this case, the user is not pressing electrode 24 against the patient's chest with sufficient force at the indicated location.

Figure 5B:
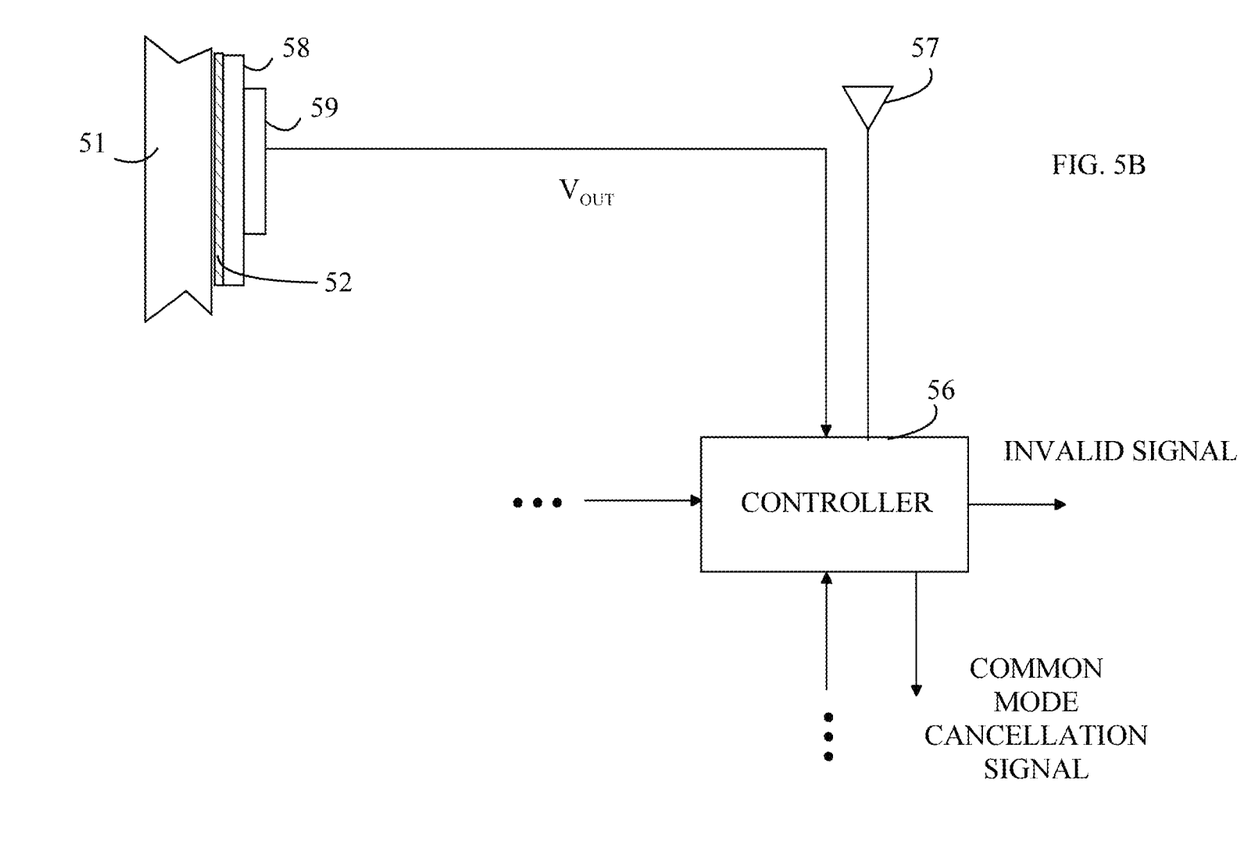
FIG. 5B illustrates the placement of one of the interface amplifiers.

In one aspect of the invention, the interface amplifiers for each electrode are placed on a small printed circuit board that is bonded directly to the electrode. Refer now to FIG. 5B, which illustrates the placement of one of the interface amplifiers. To simplify the drawing, the other electrodes and interface amplifiers that are shown in FIG. 5A have been omitted from the drawing. In this embodiment, electrode 52 is a plated metal layer on one side of a small printed circuit board 58. The interface amplifier is located in an integrated circuit 59 that is bonded to the other side of printed circuit board 58. The connection between electrode 52 and the interface amplifier are preferably made through a shielded via in printed circuit board 58. This arrangement reduces the electrical interference from AC power and other sources. As a result, the signal levels needed to detect the electrical activity on the patient's skin are substantially reduced. In fact, it has been found that signals from the electrode that contacts the chest and body can be capacitively coupled to the electrodes through a thin layer of material such as a patient's shirt. This is particularly useful for the electrode that is placed against the patient's abdomen or chest, as the patient does not need to remove the patient's shirt to make a measurement.

While the above-described embodiments utilize a small printed circuit board to hold the amplifier in close proximity to the electrode, any circuit carrier that provides a location on one side for the electrode to be attached and an integrated circuit having the amplifier on the other side of the carrier could be utilized. Accordingly, the term "printed circuit board" is defined to include any such carrier.

To complete a full twelve-lead ECG recording, a sequence of seven separate recordings must be made. The first utilizes electrode 24 against the patient's lower abdomen or leg to provide the standard lead traces, and the remaining six utilize electrode 24 against the six precordial locations on the patient's chest, with the recordings being made one at a time. To simplify the following discussion, these locations will be referred to as the recording locations. Accordingly, the system and patient must communicate to indicate the end of one recording and the beginning of the next recording.

In one aspect of the invention, the transitions between valid and invalid signals being generated are used to communicate that the position of the electrode that contacts the recording locations should be moved to the next location in a predetermined sequence. The start of each recording is marked by the transition from an invalid signal to a valid signal indication. The system then records the signals for a predetermined period of time provided the valid signal indication remains "on". After a recording of the desired length is stored with the valid signal indication being on, the system generates an invalid signal indication to inform the user to move the electrode to the next recording location in the sequence. When the systems observes a transition from an invalid signal indication to a valid signal indication, the system starts recording the signals for this location. When a valid signal is observed for the predetermined period, the process is repeated for the next recording location.

In one aspect of the invention, the valid/invalid indication is displayed to the user in a manner that does not require the user to change the positions of the user's hands on the ECG acquisition device. For example, the indication could be provided by two LEDs, one for a valid signal and the other for the invalid signal that are located near the electrode that contacts the recording locations. In another exemplary embodiment, two different tones are generated to indicate the two different signal conditions. The tones can be generated by a tone generator on the acquisition device or on the receiving processor.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. A method for operating a handheld ECG acquisition device having a plurality of receiving channels, each receiving channel comprising an electrode that is adapted for receiving electrical signals from a patient's body when said electrode is pressed against said patient's body at a predetermined location on said patient's body; said method comprising:
monitoring an output signal from each of said receiving channels for any of a plurality of invalid signal conditions during a period of time in which said output signal is being used to generate a standard lead or precordial lead trace;
signaling a user of said handheld ECG acquisition device that said handheld ECG acquisition device is improperly positioned on said patient's body; and
instructing said user on how to correct a placement of said handheld ECG acquisition device based on said invalid signal condition and said receiving channel in which said invalid signal condition was detected.

2. The method of claim 1 wherein said plurality of invalid signal conditions comprises a harmonic of AC line frequency, a constant voltage having an amplitude greater than a first threshold, or a signal strength that increases faster than a second threshold.

3. The method of claim 1 wherein instructing said user on how to correct said placement of said handheld ECG acquisition device comprises displaying a graphic of the correct placement on a display screen that is coupled to said handheld ECG acquisition device.

4. The method of claim 1 wherein instructing said user on how to correct said placement of said handheld ECG acquisition device comprises aural instructions generated by a speaker that is coupled to said handheld ECG acquisition device.

5. The method of claim 1 wherein instructing said user on how to correct said placement of said handheld ECG acquisition device comprises generating an audible tone indicating an invalid signal being detected.

6. The method of claim 1 wherein said handheld ECG acquisition device is adapted to record a plurality of tests in a predetermined sequence, each test comprising recording signals from said electrodes with one of said electrodes being located at a different point on said patient's body corresponding to that test for a predetermined recording time, and wherein said handheld ECG acquisition device detects a transition from an invalid signal to a valid signal after a previous test has been completed to signal a start of a new test in said predetermined sequence if all of said plurality of tests have not been completed.

7. An ECG recording system comprising:
a handheld ECG acquisition device characterized by a plurality of electrodes on an outer surface of said handheld ECG acquisition device, each electrode being adapted to provide an electrical connection to a corresponding location on a patient's skin when said electrode is pressed against said corresponding location, each electrode being connected to a corresponding interface circuit for amplifying an electrical signal received by said electrode to generate an output signal; and a receiving processor adapted to receive said output signal from each of said plurality of electrodes, said receiving processor monitoring each output signal for one of a plurality of invalid signal conditions and interrupting a recording of said output signals if an invalid signal is detected.

8. The ECG recording system of claim 7 wherein said receiving processor is physically connected to said handheld ECG acquisition device.

9. The ECG recording system of claim 7 wherein said receiving processor is separate from said handheld ECG acquisition device and receives said output signals by a wireless link.

10. The ECG recording system of claim 7 wherein said receiving processor generates an ECG recording selected from the group consisting of standard lead traces and precordial traces.

11. The ECG recording system of claim 7 wherein said receiving processor notifies a user if an invalid signal is detected.

12. The ECG recording system of claim 11 wherein said receiving processor provides instructions on how to correct a position of said handheld ECG acquisition device when an invalid signal is detected.

13. The ECG recording system of claim 7 wherein one of said electrodes comprises a metal layer on one surface of a printed circuit board and said interface circuit corresponding to that electrode comprises an integrated circuit mounted on another surface of said printed circuit board connected to said metal layer by a conducting via through said printed circuit board.

14. The ECG recording system of claim 7 wherein said handheld ECG acquisition device is adapted to record a plurality of tests in a predetermined sequence, each test comprising recording signals from said electrodes with one of said electrodes being located at a different point on said patient corresponding to that test for a predetermined recording time, and wherein said handheld ECG acquisition device detects a transition from an invalid signal to a valid signal after a previous test has been completed to signal a start of a new test in said predetermined sequence if all of said tests have not been completed.

\* \* \* \* \*